United States Patent [19]
Fettel et al.

[11] 3,978,863
[45] Sept. 7, 1976

[54] EXPANDING TIP EMBOLECTOMY CATHETER WITH INDICATOR BALLOON

[75] Inventors: Bruce E. Fettel, Diamond Bar; Samuel Burd, Long Beach, both of Calif.

[73] Assignees: Bruce E. Fettel, Diamond Bar; Samuel Burd, Long Beach, both of Calif.

[22] Filed: Feb. 18, 1975

[21] Appl. No.: 550,703

Related U.S. Application Data

[63] Continuation-in-part of Ser. No. 477,168, June 6, 1974, abandoned.

[52] U.S. Cl. .............. 128/348; 128/349 B; 128/DIG. 9; 128/DIG. 16
[51] Int. Cl.² ........................................ A61M 25/00
[58] Field of Search .......... 128/241, 242, 245, 246, 128/341, 342, 343, 344, 347, 348, 350, 351, DIG. 9, DIG. 16, 349

[56] References Cited
UNITED STATES PATENTS

| | | | |
|---|---|---|---|
| 1,922,084 | 8/1933 | Gerow | 128/349 B |
| 2,473,742 | 6/1949 | Auzin | 128/349 B |
| 3,467,101 | 9/1969 | Fogarty et al | 128/348 |
| 3,543,758 | 12/1970 | McWhorter | 128/349 B |
| 3,543,759 | 12/1970 | McWhorter | 128/349 BV |
| 3,599,620 | 8/1971 | Balin | 128/349 B |
| 3,799,172 | 3/1974 | Szpur | 128/349 R |

FOREIGN PATENTS OR APPLICATIONS 688,450   3/1953   United Kingdom............. 128/349 R

*Primary Examiner*—John D. Yasko
*Attorney, Agent, or Firm*—Knobbe, Martens, Olson, Hubbard & Bear

[57] ABSTRACT

A surgical catheter, exemplified in the preferred embodiment as an embolectomy catheter, which has an expandable tip, an X-ray opaque position indicator, and an expandable balloon to indicate when the expandable tip is inflated is disclosed.

17 Claims, 9 Drawing Figures

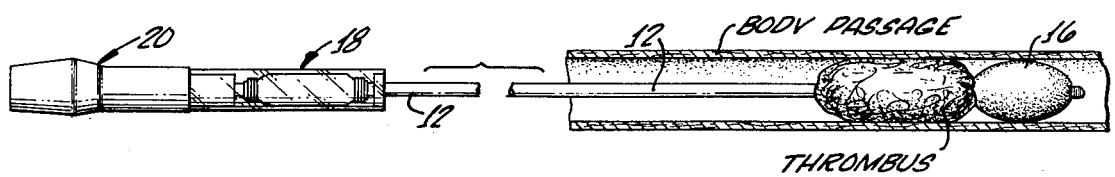
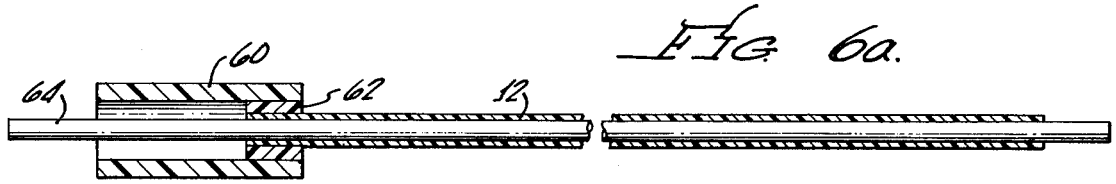
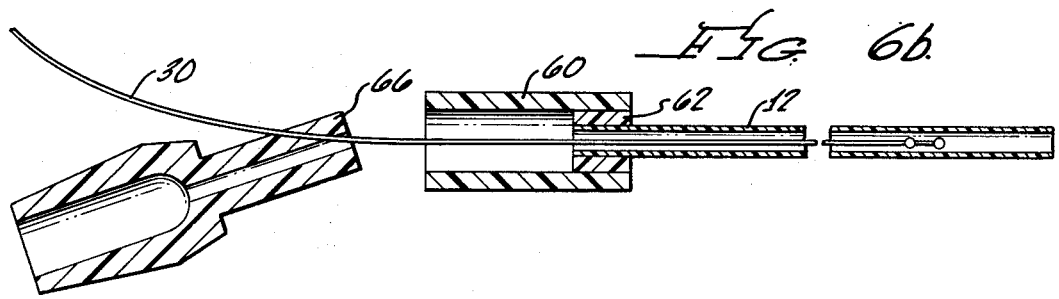
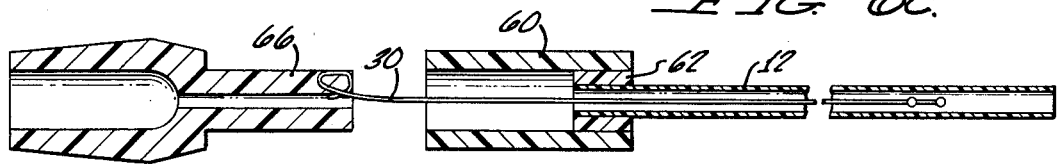
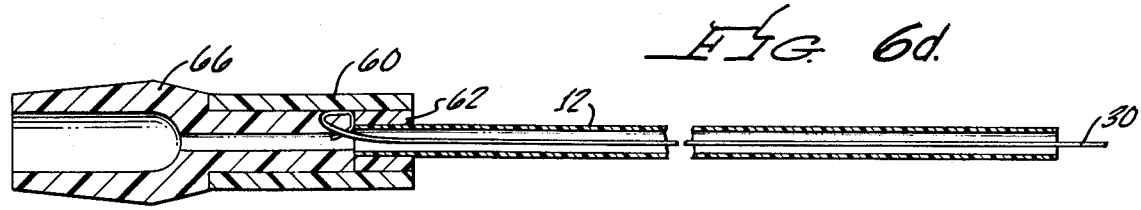

3,978,863

EXPANDING TIP EMBOLECTOMY CATHETER WITH INDICATOR BALLOON

RELATED APPLICATION

This is a continuation-in-part of Ser. No. 477,168, Filed June 6, 1974 now abandoned.

This invention relates generally to surgical catheters and, more particularly, to surgical catheters which have an expanding tip.

In the preferred embodiment, described herein as an exemplar of the invention, an embolectomy catheter having an expanding tip includes an X-ray opaque position indicator and an expandable indicator balloon.

Surgical catheters of many types are well known in the art. For example, the DePezzer surgical catheter was patented as early as Sept. 5, 1893, U.S. Pat. No. 504,424. Catheters of the various types available traditionally have an expandable portion at or near the distal end which is inserted into a body passage and expanded in various ways to accomplish particular purposes. The prior art teaches the principle of controlling the inflation of expandable tip balloon catheters, see, for example, the Foderick U.S. Pat. No. 3,211,150, issued Oct. 12, 1965.

Among the surgical catheters which have become increasingly valuable in recent years are those catheters known as embolectomy catheters. Embolectomy catheters, generally, are balloon catheters used to remove blood clots. The Fogarty U.S. Pat. No. 3,435,826 issued Apr. 1, 1969, describes one example of embolectomy catheters and discusses briefly the use of embolectomy catheters to remove clots in veins, arteries and like passages in the body. External indicators to show the inflation of an internal balloon in a urinary catheter are also known, see for example, the McWhorter U.S. Pat. No. 3,543,759, patented Dec. 1, 1970. Such catheters have generally been complex in construction and were consequently both difficult and expensive to manufacture. The prior art includes many variations and constructions of catheters, and the preceding references to specific catheters is included merely to indicate general types of catheters which have been disclosed and no comprehensive discussion of the prior art is intended.

The most commonly used prior art catheter comprises a flexible tube which has one or more apertures near its distal end. A balloon is secured near the distal end with the ends of the balloon sealed to the catheter on opposite sides of these apertures. In some of these catheters, a guidewire may be temporarily positioned through the length of the catheter in order to provide support for the catheter while it is being extended through the body passage. Otherwise, the very small flexible tube, typically having an outside diameter (O.D.) of between 0.026 and 0.092 inch, with a wall thickness in the range of about 0.004 to about 0.016 inch, tends to curl back, rather than advancing through the artery or the vein of the patient. After the tube is in place, with the prior art catheter, this guidewire is removed. In use, the surgeon passes the distal end of the balloon, in its deflated condition, through the thrombus. A fluid, such as saline, air or nitrogen, is used to expand the balloon. The catheter, with the inflated balloon on the distal end thereof, is then withdrawn, carrying with it the thrombus.

A disadvantage of prior art catheters of this type is that substantial care must be taken while inflating the balloon. A relative high inflation pressure may be required to inflate the balloon and, if the surgeon is not very careful, the balloon may be over inflated, resulting in the rupture of the balloon and the discharge of the gas or other liquid into the bloodstream of the patient. Even if the balloon does not rupture, such inflation may sufficiently enlarge the outside diameter of the balloon so as to damage the wall of the body passage in which the balloon has been inserted.

The prior art catheters do not permit the balloon to be inflated while the insertion wire is in place. As a result, the catheter is substantially transparent to X-rays and, therefore, a radio opaque solution must usually be used to inflate the balloon if the surgeon wishes to determine the position of the catheter by an X-ray technique. X-ray techniques include the use of the conventional X-ray film, with exposure made at intervals, as well as the more rapid and more dynamic display of the X-ray image on a cathode ray tube. Another disadvantage of the prior art configurations is that if the surgeon wants to reinsert the guidewire, after the catheter has been removed from the patient, the guidewire must be inserted down the length of the catheter. This is a tedious and time consuming operation because of the small dimensions of the catheter and the wire. While external indicators to permit the user to determine when the balloon at the distal tip of the catheter has been inflated are known, these constructions are usually quite complex, requiring the extrusion or other fabrication of multiple passageway catheter tubes, which may have a larger diameter than is desirable for many uses, and which may require special fittings or connectors. Even with many of the indicating type catheters in the prior art, the surgeon using the catheter has little control over the ultimate expansion of the balloon in the body passage.

The catheter of the present invention overcomes many of the technical, surgical and practical shortcomings of catheters in the prior art. One of the features of the present invention is that the catheter has extending through the length thereof an X-ray opaque wire, which may include beads or other indicia on the distal end to aid the surgeon in locating the tip of the catheter during use using conventional or other X-ray or like techniques. In the preferred embodiment, the X-ray opaque wire is connected to the catheter at its proximal end, extends through the catheter to the distal end, and is connected to the catheter tip.

Another feature of the invention is that the catheter tube may be of small diameter, including only a single passageway therethrough and may include an indicator balloon surrounded by a transparent window. The surgeon using the catheter may watch the indicator balloon through the window and determine, by the inflation of the indicator balloon, when the expandable balloon at the distal tip of the catheter has expanded into contact with the walls of the body passageway. The surgeon may inject additional gas or other fluid into the catheter to increase the pressure on the walls of the body passageway if desired.

These features, and other features which will be discussed hereinafter, result in a catheter which is more efficiently and less expensively produced than the prior art catheters, gives greater flexibility to the user in controlling the degree of inflation of the ballon distal tip of the catheter and gives the user more direct information concerning the degree of inflation of the expandable distal tip of the catheter than what is available in the catheters of the prior art.

The present invention is a biologically compatible expandable tip catheter of the type which is constructed and adapted to be inserted in and advanced through body passages, which may include veins and arteries as well as other body passages, and which is capable of being followed by X-ray techniques and which includes means to indicate to the user when the inserted expandable tip has been expanded in the body passage. The catheter structurally comprises a flexible first tube, a resilient, expandable second tube attached in fluid communication to the first tube at the distal end thereof, a resilient, expandable third tube, which is more resistant to expansion than the second tube, and which is attached in fluid communication with the first tube proximate to the proximal end of the said first tube, and a flexible, X-ray opaque element, such as a wire, extending through the catheter tubes, the tip portion of the second tube being attached proximate to the end of the opaque element. The catheter also includes means in fluid communication with the first tube for connecting the catheter to a fluid source. The fluid source may be a luer syringe, or any other fluid source selected by the surgeon. Any satisfactory source of fluid may be used, this not being a part of the present invention. The first, and second and third tubes are contructed and arranged so that when fluid pressure is applied into the catheter from the fluid source, the second tube expands first. As the second tube expands outwardly into contact with the walls of the body passage, in which it has been inserted, its outward expansion becomes limited by contact with the body passage walls. Then the third tube begins to expand outside the body and thus indicates to the user that the expandable balloon tip has been expanded inside the body and is in contact with the walls of the body passage.

The catheter of this invention, in its preferred embodiment, includes a window which extends over the third tube. The window is so constructed as to limit the outward expansion of the third tube. The second and third tubes and the window are so constructed, relative to each other, that after the third tube has expanded into contact with the window, additional fluid in the catheter causes further expansion of the second tube in the body passage, thus permitting the surgeon to apply additional pressure to the walls of the body passage, or to cause the expandable balloon at the distal end of the catheter to expand along the length of the body passage.

Another feature of the invention is that the tip of the catheter can be bent slightly to permit the introduction of torque, by means of the syringe tip to permit the catheter to be advanced through curved body passages, restrictive vessels, etc.

The construction of catheters, according to this invention, is illustrated in the drawings which are exemplary, and not limiting, of the invention and in which:

FIG. 5 is a view of the catheter, broken along its length, showing the proximal indicating balloon in its expanded condition and the relationship of the distal expandable balloon in its expanded condition for removal of an embolus; and FIGS. 6a through 6d show steps in the manufacture of the catheter of this invention.

The catheter, generally indicated at 10, is shown connected to a luer syringe 8, the latter not being part of this invention. The catheter includes a first tube 12 which may be marked with indicia 14 along the length thereof to indicate the degree of insertion, an expandable distal balloon tip indicated generally at 16, an indicating balloon assembly indicated generally at 18 which resides outside the body, and means for connecting the catheter to a fluid source indicated generally at 20.

The first tube is nearly the length of the catheter, and is constructed of a flexible, biologically compatible plastic having a diameter sufficiently small to permit it to be inserted in and advanced through body passages. The first tube may, typically, have outside diameters ranging from 0.026 inch to 0.092 inch with inside diameters ranging from 0.017 inch to 0.060 inch. The first tube 12 would typically make up from about 75 to more than 98 percent of the length of the catheter, the second and third tubes discussed hereinafter, being much shorter than this.

Figure 1:
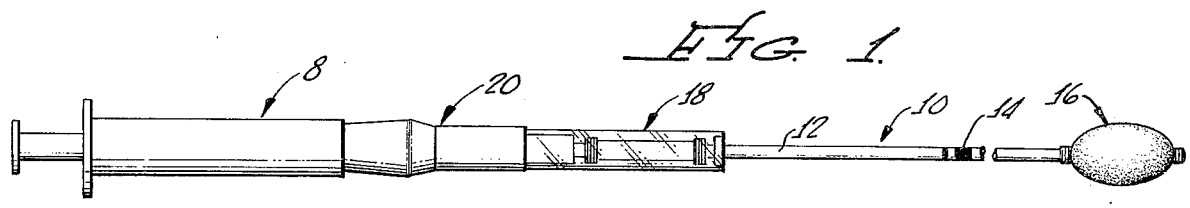
FIG. 1 is an overall view of the catheter of this invention connected to a luer syringe, the catheter tube being broken to show both ends of the catheter in a single figure.
Figure 2:
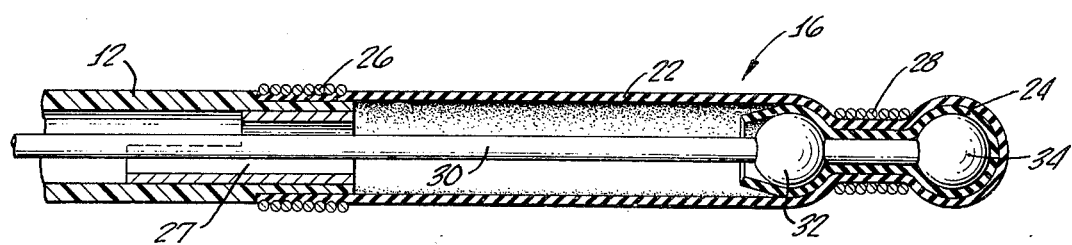
FIG. 2 is a cross-sectional view, on an enlarged scale, of the distal tip of a preferred embodiment of the invention.

The second tube, indicated in FIG. 2 by numeral 22, is approximately the same diameter as the first tube, but it is very much shorter than the first tube, typically being 1/10 or less of the length of the first tube. Like the first tube, the second tube is constructed of a biologically compatible material but, unlike the first tube, the second tube is constructed of an expandable plastic, typically a latex balloon material and may have an enclosed end, as illustrated in FIG. 2, or the end of the tube may be open, with the tip of the catheter being sealed as described hereinafter.

In the preferred construction, a second latex layer 24 is included in the distal tip of the second tube 22 to provide cushioning. The second tube is attached to the first tube in fluid communication therewith. In the exemplary embodiment, the second tube is attached to the first tube by means of a series of wraps of suture material or by a series of suture ties, indicated at 26 in FIG. 2. A reinforcing sleeve 27 prevents creep in the first tube and failure of the tie. Likewise, the distal tip of the second tube 22 is secured by suture ties 28 to the distal end of an X-ray opaque wire 30 which extends the length of the catheter and which, in the preferred embodiment illustrated, includes enlarged beads 32 and 34. The beads 32 and 34 serve a number of functions. These beads are made of an X-ray opaque material and, accordingly, show up on X-ray film on an X-ray display, indicating the location of the tip of the catheter and the expandable balloon at the tip. These beads also serve to make the attachment of the second tube to the wire more certain. In addition, these beads serve to fix the rounded shape of the end of the catheter to permit the catheter to be moved more readily through body passages. One of the features of the invention is that the wire 30 is resilient enough so that it can be coiled and handled generally without permanent deformation, but can be bent slightly and will retain the bend to permit torque to be applied to the catheter to assist the surgeon in advancing the catheter through constricted areas, curves, etc., in body passages. The suture ties 26 and 28 are, in the present fabrication process, coated with a biologically compatible epoxy resin to fix the attachment of the suture ties and of the tubes to each other and the second tube to the tip of the wire.

The indicator balloon assembly 18 comprises a third tube, which is much shorter than the first tube, but is of approximately the same diameter as the first tube, although it may be of a larger diameter, since diameter of the catheter which remains outside of the body is of less consequence than diameter of the portion of the catheter which is inserted into body passages. The third tube 36 is secured, in the illustrative example shown in the drawing, about the first tube 12 by means of suture ties 38 and 40 which may be bonded in place using epoxy resin, as discussed with respect to suture ties 26 and 28, or with other bonding material. Biological compatibility is desirable in this area of construction, simply for convenience, but is not essential since this portion of the catheter is not advanced into the body passages.

Figure 3:
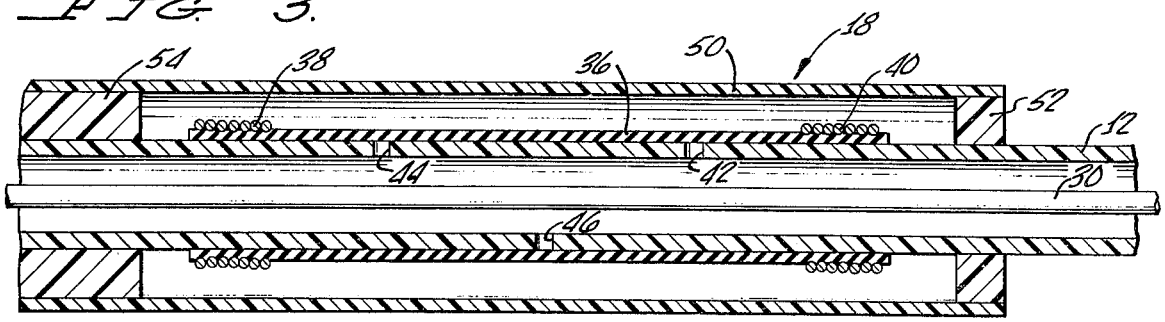
FIG. 3 is a cross-sectional view on an enlarged scale illustrating the indicating balloon and the window of the preferred embodiment of the invention, with the indicating balloon in its collapsed position.
Figure 4:
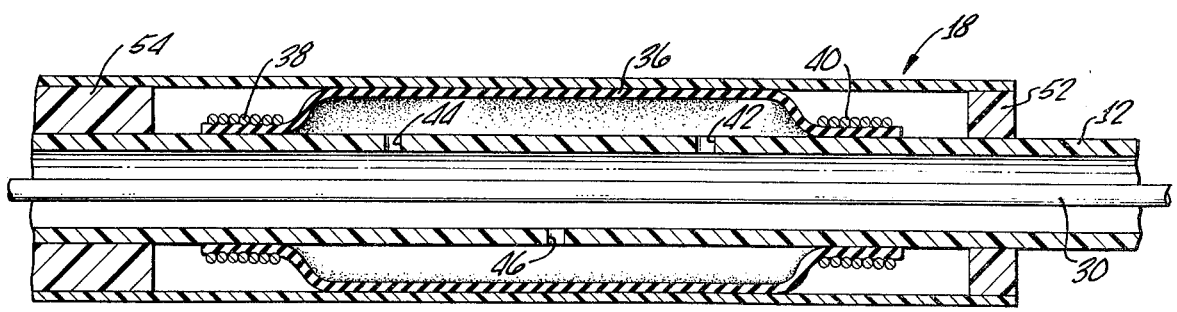
FIG. 4 is a cross-sectional view of the portion of the catheter illustrated in FIG. 3, but with the indicating balloon in its expanded condition.

The third tube is in fluid communication with the first tube by means of one or more openings in the wall, shown at 42, 44 and 46 in FIG. 3. An equivalent construction, but not preferred, would be to connect one end of the third tube to the means by which fluid is injected into the catheter and the other end of the third tube to the first tube.

The third tube, which is the indicator balloon, is surrounded by a window 50, which is preferably a transparent plastic tube extending from the connecting means toward the distal tip of the catheter so as to surround the indicator balloon. A collar 52 may be included to maintain spacing between the indicator balloon and the window. The third, indicator tube is typically less than 1/10 the length of the first tube and, when in collapsed configuration, is spaced from the window. The window extends over the third tube to permit the third tube to be viewed by the user. The window also limits the outward expansion of the third tube during use. The window and the second and the third tubes are so constructed and disposed relative to each other and are made of material such that upon injection of fluid into the catheter the second tube expands first until further outward expansion of the second tube is limited by its contact with the resistance of further expansion of the body passage in which the distal balloon is disposed. Thereafter, the third tube expands until outward expansion of the third, indicator tube, is limited by the window. Thereafter, additional fluid injected into the catheter causes the second tube to expand further in the body passage.

Catheters made according to this invention will typically have a predetermined maximum volume capacity which will be greater than the sum of the volume of the first tube, the volume of the second tube in its initially expanded condition, and the third tube in its expanded condition. The surgeon, thus, has the choice of expanding the first balloon so that it is in contact with and its expansion is constrained by the walls of the body passage. This is indicated when the second balloon expands. If further pressure is desired in the body passage, the surgeon can inject additional fluid, after the indicator balloon has been fully expanded, into the distal tip balloon, up to the maximum volume capacity of the catheter.

FIG. 5 illustrates the use of the embolectomy catheter embodiment of this invention, which has been described here as being typical of catheters built according to the principles set forth herein. The catheter is inserted into the body passage and is advanced along the passage through the thrombus.

One preferred procedure for manufacturing the luer syringe connector 20 and attaching it to the catheter is illustrated generally in FIGS. 6a through 6d. The proximal end of the first tube 12 is permanently bonded to outer and inner bushings 60 and 62, using a suitable adhesive, the epoxy adhesives being most satisfactory generally. A mandrel 64 may be used during this bonding procedure to prevent the entry of any adhesive into the inside of the tube 12. The mandrel is removed and one or more holes, for example, as illustrated in FIG. 3, are drilled in the wall of the first tube 12. Because of the scale of the drawings in FIG. 6, these holes are not illustrated. The wire 30 is inserted through the entire length of the catheter and through the stem wall of the luer syringe connector 66, which has been previously drilled with a slanting hole, as indicated in FIG. 6b. The wire is then bent in the form of a loop as shown in FIG. 6c and the stem wall of connector 66 is coated with an adhesive and inserted in the sleeve 60 where it is permanently bonded. The wire 30 then extends through the entire length of the catheter, being connected to the fluid connecting means at the proximal end, as illustrated in FIG. 2, to the expandable balloon at the distal end of the catheter. The beads 32 and 34 may be formed on the wire before assembly, and the appropriate length of wire selected, or following the assembly illustrated in FIG. 6. The assembly of the indicator balloon and the distal tip balloon has been discussed before and is not illustrated in FIG. 6, because of the scale of these drawings.

Suitable materials for constructing embolectomy catheters and other surgical catheters are well known in the art, and no extended discussion is warranted. Generally speaking, stainless steels are satisfactory for fabricating the wire 30, No. 302 stainless steel wire being quite suitable. Actually, the material of construction of the stainless steel wire is not as important in terms of biological compatibility, as are the materials of the construction of the first and second tubes, inasmuch as the wire is not in continuous contact with body fluids and tissues and in most circumstances, would not contact body fluids or tissues at all. It should, of course, be non-corrosive and is necessarily X-ray opaque if it is to be used as a position indicator using X-ray techniques.

The first tube may be made of any of a large number of biologically compatible polymers. Most conventional polymers are sufficiently compatible for temporary use in the body and long term compatibility is not required. The poly olefins, polyvinylchloride, polyethylenes, the polyacetals, poly-butadienestyrene copolymers, the polyfluoro and polyfluorochloro-polymers, such as TEFLON and KEL-F and other well known polymers and copolymers are generally suitable, when properly processed and handled for at least temporary residence in the body.

The medical literature on prosthetic devices gives numerous examples of materials which have been found to be suitable for either short term or long term compatibility with the body fluids and tissues. Selection of particular materials will depend upon the type of surgical catheter being designed. For example, a different degree and type of compatibility would be required for an embolectomy catheter than would be required for an in-dwelling urinary catheter, a gastrointestinal catheter, an endotracheal catheter, etc.

The balloon is made of a strong elastic material, such as latex rubber or plastic elastomers, which will expand outwardly when unconfined. The third tube, which is the indicator balloon, may be constructed of a different material than the second tube such that the third tube is more resistant to outward expansion, upon application of internal fluid pressure, than is the second tube. The third tube may, however, be made of the same material as the second tube, but made with thicker walls to obtain a higher degree of resistance to outward expansion than the second tube. Wall thickness of the latex balloon tubes may vary quite considerably from, for example, less then 0.005 inch to more than 0.02 inch, the thickness of the third tube wall being greater than the thickness of the first tube wall by a factor of, for example, 1.5 to 5.0, where wall thickness differences are relied upon to obtain differential expansion.

One of the particular features and advantages of catheters constructed according to this invention is that they may be shipped in smaller containers than is normally possible with most of the prior art catheters, which embody an unsupported plastic tube. Since plastic catheters, if not supported by a guidewire within, will take a permanent set when coiled, these catheters typically must be packaged and shipped in a flat condition. This requires long, bulky packages, with increased risk of damage during shipment. Storage of catheters in large numers also occupies a great deal of valuable space, which is nearly always limited in hospitals. In contrast, the catheter of this invention can be coiled and shipped in small boxes, since the guidewire does not take a permanent set when coiled, as distinguished from a more sharp bend, and any set or deformation in the plastic has little if any effect upon the characteristics of the catheter during use.

Another feature of this invention is that in the event of over inflation and rupture of the expandable distal end balloon, an occurrence which is less likely with the present catheter than those of the prior art because of the indicator feature of the catheter, the plastic tubing material and the latex remain integral and coherent, attaching itself to the wire, thus reducing the possibility of a foreign plastic particle being left in the body when the catheter is withdrawn.

Although these advantages and other advantages discussed herein are most applicable to the embolectomy version of catheters of this invention, the invention is not so restricted. It is contemplated that the scope of this invention not be limited to embolectomy catheters and that a reasonable range of equivalents in materials, constructions, techniques and features, consistent with the advantages and characteristics discussed herein, be included within the scope of the invention, as defined in the following claims.

What is claimed is:

1. A biologically compatible expandable tip embolectomy catheter of the type constructed and adapted to be inserted in and advanced through blood passages, which is capable of being followed by X-ray techniques and which includes means to indicate to the user when the inserted expandable tip has been expanded in the body passage, comprising:

a flexible first tube;

a resilient, expandable second tube adapted to engage the thrombus, attached in fluid communication with the first tube at the distal end thereof, the distal end of said second tube being sealed;

a resilient, expandable third tube, which is more resilient to expansion than the second tube, attached in fluid communication with the first tube proximate to the proximal end of the first tube;

means for limiting the expansion of said third tube;

a flexible, X-ray opaque element extending through said tubes, the tip portion of the second tube being attached proximate the end of the opaque element; and means in fluid communication with the first tube for connecting the catheter to a fluid source, for applying fluid pressure into the catheter from a fluid source to expand the second tube outwardly into contact with the walls of the body passage in which it has been inserted first, then to expand the third tube outside the body until such expansion is empeded by said limiting means to indicate to the user that the expandable tip has been expanded inside the body, and then to expand the second tube further to press against the walls of the body passage.

2. The catheter defined in claim 1 wherein said limiting means comprises:

a window extending over the third tube, for limiting the outward expansion of the third tube, and for causing further expansion of the second tube in the body passage upon application of further fluid pressure after the third tube has expanded into contact with the window.

3. The catheter as defined in claim 1 wherein:

the limiting means is a clear plastic tube encircling and extending about the third tube, said clear plastic tube constituting a window which is normally spaced from the third tube when the latter is in uninflated condition, and being so constructed and disposed as to restrain the third tube from unlimited expansion.

4. A biologically compatible expandable embolectomy catheter of the type constructed and adapted to be inserted in and advanced through blood passages, which includes means to indicate to the user when the inserted expandable tip has been expanded in the body passage, comprising:

a first elongate tube, constructed of flexible, biologically compatible plastic having an outside diameter less than 0.1 inches to permit it to be inserted in and advanced through body passages;

a second tube, adapted to engage the thrombus which is shorter than the first tube but is approximately the same diameter as the first tube, constructed of a biologically compatible expandable plastic and sealed at the distal end of said first elongate tube and in fluid communication therewith;

a third tube, which is shorter than the first tube but is of approximately the same diameter as the first tube, constructed of an expandable plastic which is more resistant to expansion under fluid pressure than the second tube, said third tube sealed to the proximal end of said first tube and in fluid communication therewith;

means for connecting the proximal end of the first tube to a source of fluid for injection into the catheter for injection of a first quantity of fluid into the catheter to first expand the second tube until further outward expansion of the same is limited by the walls of the body passage in which it is disposed and thereafter to expand the third tube, which is outside the body and visible during use, to thereby indicate to the user that the second tube in the body passage has been limited by the body passage;

means for limiting the expansion of said third tube for providing further expansion of said second tube against said walls of said body passage in response to injection of a second, subsequent quantity of fluid into the catheter; and a flexible, X-ray opaque wire extending through said tubes, the tip portion of the second tube being attached proximate the end of the opaque wire.

5. The catheter defined in claim 4 wherein said expansion limiting means comprises:

a window extending over the third tube to permit viewing of the third tube by the user and to limit the outward expansion of the same during use.

6. The catheter defined in claim 4 wherein:

the wire includes means proximate the distal tip thereof which are X-ray opaque for distinguishing the tip of the wire from the remainder of the wire by X-ray techniques.

7. The catheter defined in claim 6 wherein said expansion limiting means comprises:

a window extending over the third tube to permit viewing of the third tube by the user and to limit the outward expansion of the same during use.

8. The catheter defined in claim 7 wherein:

the second tube is secured at the distal tip of the first tube and extends beyond said tip, the distal end of the second tube being secured to the end of the wire.

9. The catheter defined in claim 8 wherein:

the window is a transparent tube extending from proximate the proximal end of the catheter toward the distal end thereof a distance sufficient to surround the third tube.

10. The catheter defined in claim 9 wherein:

the third tube is secured at each end thereof to and surrounds the first tube and the first tube has at least one opening in the wall thereof for permitting fluid communication between the first and third tubes.

11. The catheter defined in claim 7 wherein:

the window is a transparent tube extending from proximate the proximal end of the catheter toward the distal end thereof a distance sufficient to surround the third tube.

12. The catheter defined in claim 7 wherein:

the wire can be bent slightly near the distal end thereof and will retain a slight bend to permit the catheter to be advanced through restrictive or curved body passages.

13. A method of using a biologically compatible expandable tip embolectomy catheter of the type constructed and adapted to be inserted in and advanced through blood passages and which includes an elongate tube in fluid communication with an expandable portion near the distal end and an expandable portion near the proximal end, said elongate tube open at the proximal end for the application of fluid thereto and sealed at the distal end, said distal end expandable portion expanding more easily than said proximal end expanding portion and means for limiting expansion of the proximal end expanding portion, comprising the steps of:

inserting said distal end and a length of said elongate tube into a blood passage;

applying fluid under pressure to said open proximal end to expand said distal end expanding portion into contact with said blood passage;

applying additional fluid under pressure to said open proximal end to expand said proximal end expanding portion and thus notify the operator of contact between said distal end expanding portion with said blood passage; and continuing to apply additional fluid until further expansion of said proximal end expanding portion is impeded by said limiting means.

14. A method of using a catheter as defined in claim 13, additionally comprising the step of:

applying additional fluid under pressure to said open proximal end after expansion of said proximal end expanding portion is limited to further expand said distal end expanding portion against said blood passage.

15. A method of using an embolectomy catheter as defined in claim 13, wherein an X-ray opaque element extends through the tubes, and additionally comprising:

monitoring said inserting step with X-rays.

16. A method of using an embolectomy catheter as defined in claim 13 wherein said inserting step includes:

passing the distal end of said catheter through a thrombus in said blood passage.

17. A biologically compatible expandable tip embolectomy catheter of the type constructed and adapted to be inserted in and advanced through blood passages, which includes means to indicate to the user when the inserted expandable tip has been expanded in the body passage, comprising:

a flexible first tube;

a resilient, expandable, second tube adapted to engage the thrombus attached in fluid communication with the first bue proximate to the distal end thereof, the distal end of said second tube being sealed;

a resilient, expandable third tube, which is more resistant to expansion than the second tube, attached in fluid communication with the first tube proximate to the proximal end of the first tube;

means in fluid communication with the first tube for connecting the catheter to a fluid source, for applying fluid pressure into the catheter from a fluid source to expand the second tube outwardly into contact with the walls of the body passage in which it has been inserted first and then to expand the third tube outside the body to indicate to the user that the expandable tip has been expanded inside the body; and means normally outside the body for indicating a predetermined expansion of the third tube.

* * * * *

UNITED STATES PATENT OFFICE
CERTIFICATE OF CORRECTION

PATENT NO. : 3,978,863
DATED : September 7, 1976
INVENTOR(S) : Bruce E. Fettel -- Samuel Burd It is certified that error appears in the above-identified patent and that said Letters Patent are hereby corrected as shown below:

Column 3, Line 28, "contructed" should be --constructed--

Column 10, Line 46, "bue" should be --tube--

Signed and Sealed this

Fourteenth Day of December 1976

[SEAL]

Attest:

RUTH C. MASON
*Attesting Officer*

C. MARSHALL DANN
*Commissioner of Patents and Trademarks*